United States Patent [19]

Hagan et al.

[11] Patent Number: 4,654,624

[45] Date of Patent: Mar. 31, 1987

[54] GAS SENSOR

[75] Inventors: Werner Hagan, Bad Schwartau; Johannes Lagois, Lübeck, both of Fed. Rep. of Germany

[73] Assignee: Drägerwerk Aktiengesellschaft, Lübeck, Fed. Rep. of Germany

[21] Appl. No.: 827,073

[22] Filed: Feb. 6, 1986

[30] Foreign Application Priority Data

Feb. 9, 1985 [DE] Fed. Rep. of Germany ....... 3504498

[51] Int. Cl.$^4$ ............................................... H01L 7/00
[52] U.S. Cl. ......................................... 338/34; 338/25
[58] Field of Search ................... 338/34, 35, 25, 22 R, 338/22 SD; 73/23, 27 R; 422/94, 98; 204/426

[56] References Cited

U.S. PATENT DOCUMENTS

| | | | |
|---|---|---|---|
| 4,007,435 | 2/1977 | Tien | 338/34 |
| 4,443,781 | 4/1984 | Ohta et al. | 338/34 |
| 4,453,151 | 6/1984 | Leary et al. | 338/34 |
| 4,469,626 | 9/1984 | Tuohig et al. | 338/34 X |

Primary Examiner—E. A. Goldberg
Assistant Examiner—M. Lateef
Attorney, Agent, or Firm—Walter Ottesen

[57] ABSTRACT

A gas sensor has a plurality of sensor elements disposed on a common supporting substrate and a heating arrangement for generating the operating temperature necessary for measurement. The gas sensor unites sensor elements, which furnish desired measured quantities in different ways, on a common substrate while minimizing the heating capacity as much as possible and with a maximum possible sensitivity of response. To this end, a first group of sensors are configured as thin-film semiconductor sensors and a second group of sensor elements are disposed on a narrowed portion of the supporting substrate. Both groups of sensors are disposed on the same surface of the supporting substrate.

8 Claims, 1 Drawing Figure

U.S. Patent      Mar. 31, 1987      4,654,624
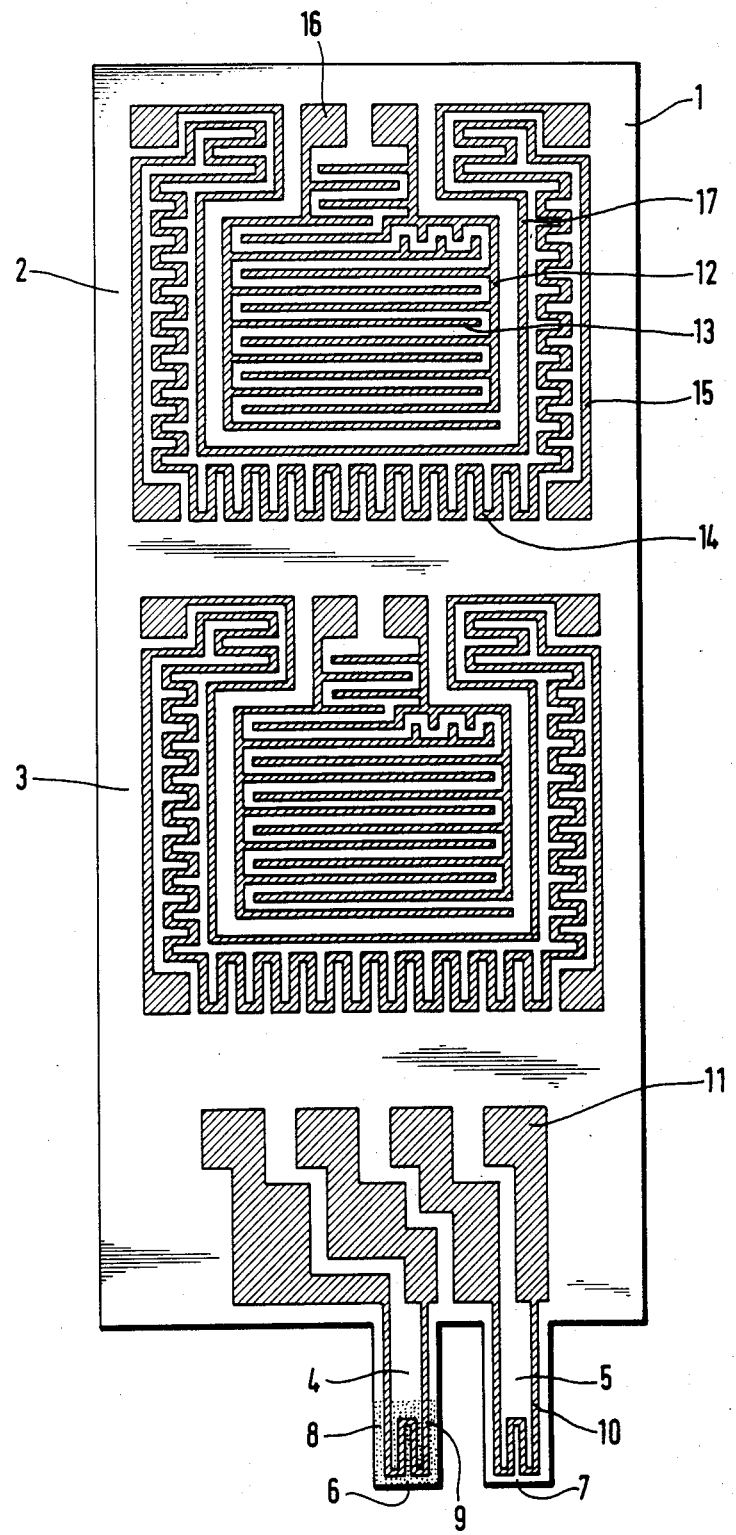

GAS SENSOR

FIELD OF THE INVENTION

The invention relates to a gas sensor having a plurality of sensor elements disposed on a common substrate, a heating device for generating the operating temperature necessary for measurement, and temperature sensors.

BACKGROUND OF THE INVENTION

A sensor of this general type is known from U.S. Pat. No. 4,007,435.

The known gas sensor has a first supporting substrate to which a heating device is applied, and a second supporting substrate on which various sensor elements are disposed. Both the heating device and the sensor elements are provided with suitable contacts and conductor leads as electrical connections. For operation, both substrates are placed in close contact with one another, so that the lower substrate having the heating device heats the substrate located thereabove, having the sensor elements, to the operating temperature required for the measurement. Since the sensor elements are used for detecting gas components, for instance in automobile exhaust, their surfaces must be exposed freely to the gas flow, and so no other arrangement of the substrate is possible. If the known gas sensor were expanded by using further sensor elements, the second supporting substrate would be enlarged further, which would result in a corresponding enlargement of the first supporting substrate having the heating device.

Because of the large surface area in the layer-like configuration of the known gas sensor, relatively high heating capacities are needed to heat the sensor elements to their operating temperature or to keep them at that temperature, once the latter is attained.

Furthermore, with the known arrangement it is not possible to dispose heat-tone sensors (pellistors), for example, on the second substrate that carries the sensor elements, because the relatively large mass of the supporting substrate means that the temperature changes, which in such cases are only slight, can no longer be detected because of heat dissipation.

SUMMARY OF THE INVENTION

It is the object of the invention to improve a gas sensor of the above-mentioned type such that a plurality of sensor elements operating on various measurement principles, such as semiconductor sensors or pellistors, are disposed on a common substrate, the sensors being exposed to the gas mixture that is to be investigated. The heating capacity needed for generating the operating temperatures is reduced and the response speed of the pertinent sensors is increased because the mass of the sensor material and supporting substrate has been reduced.

This object is attained by disposing the sensor elements on one side of the supporting substrate in the form of thin-film semiconductor sensors and disposing further sensor elements on a narrowed portion of the substrate.

The advantages of the invention are that the sensor elements, which are configured in the form of thin-film semiconductor sensors, require only an inherently thin-walled supporting substrate, and their configuration can be adapted arbitrarily in contour and size to existing requirements. All the contact surfaces for supplying electrical voltage or emitting signals can be integrated into the semiconductor sensor. The sensor disposed on the narrowed portion of the substrate is substantially thermally insulated from the substrate material surrounding it so that a signal can be detected virtually without interference by the other semiconductor sensors.

It has been particularly advantageous to dispose heat-tone sensors on the narrowed portion of the substrate, because they are then thermally insulated from the other sensors.

In a further embodiment of the invention, the heat-tone sensors can be applied to tongue-like extensions on one end of the substrate. This increases their thermal insulation still further and reduces the heating capacity needed.

Advantageously, the heat-tone sensors can, as a measuring element, be provided with a catalyst or else can be configured as a catalyst-free reference element. Because of the disposition of these sensors adjacent each other, measurement signals can thus be evaluated with greater accuracy. It is likewise possible for various heat-tone sensors to be provided with respectively different catalysts to permit detecting different gas components simultaneously.

To increase the heat emission to the sensor elements and to decrease the heating capacity required therefor, the conductor paths on the portion of the sensor elements that are sensitive for detection are disposed in meandering fashion or are arbitrarily intertwined. The electrodes of the semiconductor sensors are suitably configured as interdigitating combs.

BRIEF DESCRIPTION OF THE DRAWING

The invention will now be described with reference to the drawing which shows a plan view of the gas sensor according to the invention.

DESCRIPTION OF THE PREFERRED EMBODIMENT OF THE INVENTION

In the drawing, two semiconductor sensors 2 and 3 are provided on a supporting substrate 1, and heat-tone sensors 6 and 7 are disposed on the tongue-like extension pieces 4 and 5, respectively. The semiconductor sensors 2 and 3 have interdigitating electrodes 12 and 13, which are surrounded by meanderingly intertwined heating conductor paths 14 and 15 as well as by a temperature sensor 17. The contact surfaces 16 for the electrodes 12, 13, the heating conductor paths 14, 15 and the temperature sensor 17 are likewise applied to the supporting substrate 1.

Of the heat-tone sensors 6 and 7, one is provided with a catalyst 8. The sensors 6 and 7 have respective meandering heating conductor paths 9 and 10 on their respective portions that are sensitive for detection. The heating conductor paths 9 and 10 terminate in respective contact surfaces 11 configured to have large surface areas on the supporting substrate 1.

It is understood that the foregoing description is that of the preferred embodiments of the invention and that various changes and modifications may be made thereto without departing from the spirit and scope of the invention as defined in the appended claims.

What is claimed is:

1. A gas sensor comprising:

a supporting substrate having a main portion and a narrowed portion extending from and being integral with said main portion;

first gas sensor means configured as thin-film semiconductor sensor means and mounted on said main portion;

temperature sensing means disposed on said main portion;

heating means disposed on a surface of said supporting substrate for imparting heat to said first sensor means so as to raise the temperature thereof to a level effective for making measurements; and, second gas sensor means mounted on said narrowed portion; said first and second sensors and said heating means being on said surface.

2. The gas sensor of claim 1, said second sensor means being a plurality of second sensors configured as respective heatable heat-tone sensors.

3. The gas sensor of claim 1, said second sensor means being a plurality of second sensors; and, said main portion having an end and said narrowed portion being a tongue-like extension extending from said end of said main portion, said substrate having a further tongue-like extension disposed adjacent said first-mentioned tongue-like extension; and, said second sensors being arranged on corresponding ones of said tongue-like extensions.

4. The gas sensor of claim 2, one of said heat-tone sensors having a catalyst and being a measuring element and another one of said heat-tone sensors having no catalyst and being a reference sensor.

5. The gas sensor of claim 2, said main portion having an end and said narrowed portion being a tongue-like extension extending from said end of said main portion, said substrate having a further tongue-like extension 35 disposed adjacent said first-mentioned tongue-like extension; and, said heat-tone sensors being arranged on corresponding ones of said tongue-like extensions, said gas sensor further comprising additional heating means for imparting heat to said heat-tone sensors, said additional heating means including meander-like conductive paths arranged on corresponding ones of said tongue-like extensions and having respective contact surface means on said main portion.

6. The gas sensor of claim 1, said first sensor means being a plurality of thin-film sensors each having a comb-like electrode, said thin-film sensors being arranged on said main portion so as to cause said comb-like electrodes of said sensors to be interdigitated with respect to each other; and, said first-mentioned heat means including a heating conductor path configured so as to be interdigitated upon itself, and a temperature sensor arranged on said main portion for detecting the temperature of said thin-film sensors.

7. A gas sensor device comprising:

a supporting substrate having a main portion and a narrowed portion integral with said main portion;

first gas sensor means configured as thin-film semiconductor sensor means and mounted on said main portion;

temperature sensing means disposed on said main portion;

heating means disposed on said supporting substrate for imparting heat to said first sensor means so as to raise the temperature thereof to a level effective for making measurements;

said narrowed portion having a finger-like configuration and extending outwardly from said main portion so as to be substantially thermally insulated from said heat imparted to said main porion; and, second gas sensor means mounted on said narrowed portion of said supporting substrate so as to permit said second gas sensor means to operate virtually without interference from said heat.

8. The gas sensor of claim 7, said second gas sensor means being configured as a heatable heat-tone sensor.

* * * * *

UNITED STATES PATENT AND TRADEMARK OFFICE
CERTIFICATE OF CORRECTION

PATENT NO. : 4,654,624

DATED : March 31, 1987

INVENTOR(S) : Werner Hagen and Johannes Lagois

It is certified that error appears in the above-identified patent and that said Letters Patent is hereby corrected as shown below:

On the front page in the heading: delete "Hagan et al" and substitute -- Hagen et al -- therefor.

On the front page, under Inventors, delete "Werner Hagan" and substitute -- Werner Hagen -- therefor.

In column 4, line 32: delete "porion;" and substitute -- portion; -- therefor.

Signed and Sealed this

Eleventh Day of August, 1987

Attest:

DONALD J. QUIGG

Attesting Officer

Commissioner of Patents and Trademarks